United States Patent
Huey et al.

(10) Patent No.: US 8,557,278 B2
(45) Date of Patent: *Oct. 15, 2013

(54) DEVICES AND METHODS FOR THE DELIVERY OF BLOOD CLOTTING MATERIALS TO BLEEDING WOUNDS

(75) Inventors: Raymond J. Huey, Orange, CT (US); Jeffrey L. Horn, Rocky Hill, CT (US)

(73) Assignee: Z-Medica, LLC, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/595,932

(22) Filed: Aug. 27, 2012

(65) Prior Publication Data

US 2013/0041332 A1 Feb. 14, 2013

Related U.S. Application Data

(63) Continuation of application No. 11/592,477, filed on Nov. 2, 2006, now Pat. No. 8,252,318, which is a continuation-in-part of application No. 11/054,918, filed on Feb. 9, 2005, now abandoned.

(51) Int. Cl.
| | |
|---|---|
| *A61L 15/14* | (2006.01) |
| *A61L 15/16* | (2006.01) |
| *A61L 15/18* | (2006.01) |
| *A61K 9/14* | (2006.01) |
| *A61F 13/00* | (2006.01) |

(52) U.S. Cl.
USPC ........... 424/445; 424/444; 424/489; 424/446; 424/447; 602/42; 602/43; 602/45; 602/46; 602/53

(58) Field of Classification Search
USPC ............ 424/445, 444, 489, 446, 447; 602/42, 602/43, 45, 46, 53, 57; 502/80
See application file for complete search history.

(56) References Cited

U.S. PATENT DOCUMENTS

| 2,688,586 A | 9/1954 | Eberl et al. |
| 2,969,145 A | 1/1961 | Hannuer, Jr. |

(Continued)

FOREIGN PATENT DOCUMENTS

| CA | 1223208 | 6/1987 |
| CN | 1970090 A | 5/2007 |

(Continued)

OTHER PUBLICATIONS

Top, Ayben et al. "Silver, zinc, and copper exchange in a Na—clinoptilolite and resulting effect on antibacterial activity." Applied Clay Science. 2004. pp. 13-19. vol. 27.

(Continued)

*Primary Examiner* — Savitha Rao
(74) *Attorney, Agent, or Firm* — Knobbe Martens Olson & Bear LLP

(57) ABSTRACT

An apparatus for promoting the clotting of blood and controlling bleeding comprises a receptacle for retaining blood clotting material in particulate form therein. A pad for controlling bleeding comprises a mesh structure and a support attached to the mesh structure to facilitate the application of pressure to the pad and the wound. A bandage applicable to a bleeding wound comprises a mesh structure and a flexible substrate attached to the mesh structure, the substrate being a cloth or plastic member that may be adhesively attachable to cover a wound. In any embodiment, at least a portion of the receptacle or mesh structure is defined by a mesh having openings therein, and at least a portion of the particulate blood clotting material is in direct contact with blood. The mesh may include a zeolite powder impregnated or otherwise incorporated therein.

22 Claims, 4 Drawing Sheets

(56) References Cited

U.S. PATENT DOCUMENTS

| | | |
|---|---|---|
| 3,122,140 A | 2/1964 | Crowe et al. |
| 3,181,231 A | 5/1965 | Breck |
| 3,189,227 A | 6/1965 | Hobbs et al. |
| 3,366,578 A | 1/1968 | Michalko |
| 3,386,802 A | 6/1968 | Michalko |
| 3,538,508 A | 11/1970 | Young |
| 3,550,593 A | 12/1970 | Kaufman |
| 3,723,352 A | 3/1973 | Warner et al. |
| 3,763,900 A | 10/1973 | Solms-Baruth et al. |
| 3,979,335 A | 9/1976 | Golovko et al. |
| 4,373,519 A | 2/1983 | Errede et al. |
| 4,374,044 A | 2/1983 | Schaefer et al. |
| 4,379,143 A | 4/1983 | Sherry et al. |
| 4,435,512 A | 3/1984 | Ito et al. |
| 4,460,642 A | 7/1984 | Errede et al. |
| 4,514,510 A | 4/1985 | Alexander |
| 4,524,064 A | 6/1985 | Nambu |
| 4,525,410 A | 6/1985 | Hagiwara et al. |
| 4,569,343 A | 2/1986 | Kimura et al. |
| 4,626,550 A | 12/1986 | Hertzenberg |
| 4,631,845 A | 12/1986 | Samuel et al. |
| 4,651,725 A | 3/1987 | Kifune et al. |
| 4,728,323 A | 3/1988 | Matson |
| 4,748,978 A | 6/1988 | Kamp |
| 4,822,349 A | 4/1989 | Hursey et al. |
| 4,828,081 A | 5/1989 | Nordstrom et al. |
| 4,828,832 A | 5/1989 | DeCuellar et al. |
| 4,911,898 A | 3/1990 | Hagiwara et al. |
| 4,938,958 A | 7/1990 | Niira et al. |
| 4,956,350 A | 9/1990 | Mosbey |
| 5,140,949 A | 8/1992 | Chu et al. |
| 5,146,932 A | 9/1992 | McCabe |
| 5,474,545 A | 12/1995 | Chikazawa |
| 5,486,195 A | 1/1996 | Myers et al. |
| 5,502,042 A | 3/1996 | Gruskin et al. |
| 5,538,500 A | 7/1996 | Peterson |
| 5,556,699 A | 9/1996 | Niira et al. |
| 5,578,022 A | 11/1996 | Scherson et al. |
| 5,597,581 A | 1/1997 | Kaessmann et al. |
| 5,599,578 A | 2/1997 | Butland |
| D386,002 S | 11/1997 | Hinkle |
| 5,696,101 A | 12/1997 | Wu et al. |
| 5,716,337 A | 2/1998 | McCabe et al. |
| 5,725,551 A | 3/1998 | Myers et al. |
| 5,728,451 A | 3/1998 | Langley et al. |
| 5,766,715 A | 6/1998 | Garconnet |
| 5,788,682 A | 8/1998 | Maget |
| 5,801,116 A | 9/1998 | Cottrell et al. |
| 5,826,543 A | 10/1998 | Raymond et al. |
| 5,855,570 A | 1/1999 | Scherson et al. |
| 5,916,511 A | 6/1999 | Kotani et al. |
| 5,941,897 A | 8/1999 | Myers |
| 5,964,239 A | 10/1999 | Loux et al. |
| 5,964,349 A | 10/1999 | Odagiri |
| 5,981,052 A | 11/1999 | Sugiyama |
| 5,993,964 A | 11/1999 | Nakajima |
| 6,037,280 A | 3/2000 | Edwards et al. |
| 6,060,461 A | 5/2000 | Drake |
| 6,086,970 A | 7/2000 | Ren |
| 6,123,925 A | 9/2000 | Barry et al. |
| 6,159,232 A | 12/2000 | Nowakowski |
| 6,187,347 B1 | 2/2001 | Patterson et al. |
| 6,203,512 B1 | 3/2001 | Farris et al. |
| 6,251,423 B1 | 6/2001 | Bradford |
| 6,372,333 B1 | 4/2002 | Sugiyama et al. |
| 6,428,800 B2 | 8/2002 | Greenspan et al. |
| 6,450,537 B2 | 9/2002 | Norris |
| 6,475,470 B1 | 11/2002 | Kayane et al. |
| 6,481,134 B1 | 11/2002 | Aledo |
| 6,486,285 B2 | 11/2002 | Fujita |
| 6,495,367 B1 | 12/2002 | Isogawa et al. |
| 6,523,778 B2 | 2/2003 | Key et al. |
| 6,573,419 B2 | 6/2003 | Naimer |
| 6,590,337 B1 | 7/2003 | Nishikawa et al. |
| 6,622,856 B2 | 9/2003 | Gallo et al. |
| 6,630,140 B1 | 10/2003 | Grunstein |
| 6,685,227 B2 | 2/2004 | Merry et al. |
| 6,700,032 B1 | 3/2004 | Gray |
| 6,701,649 B1 | 3/2004 | Brosi |
| 6,745,720 B2 | 6/2004 | Rasner et al. |
| 6,890,177 B2 | 5/2005 | Dragan |
| 6,998,510 B2 | 2/2006 | Buckman et al. |
| 7,125,821 B2 | 10/2006 | Xu et al. |
| 7,303,759 B2 | 12/2007 | Mershon |
| 7,371,403 B2 | 5/2008 | McCarthy et al. |
| 7,429,252 B2 | 9/2008 | Sarangapani |
| 7,595,429 B2 | 9/2009 | Hursey |
| 7,604,819 B2 | 10/2009 | Huey et al. |
| 7,825,133 B2 | 11/2010 | Yi |
| 7,858,123 B2 | 12/2010 | Stucky |
| 7,968,114 B2 | 6/2011 | Huey et al. |
| 8,063,264 B2 | 11/2011 | Spearman et al. |
| 8,114,433 B2 | 2/2012 | Huey et al. |
| 8,202,532 B2 | 6/2012 | Huey et al. |
| 8,252,318 B2 | 8/2012 | Huey et al. |
| 8,252,344 B2 | 8/2012 | Hursey |
| 8,257,731 B2 | 9/2012 | Horn et al. |
| 8,257,732 B2 | 9/2012 | Huey et al. |
| 8,277,837 B2 | 10/2012 | Fischer et al. |
| 8,383,148 B2 | 2/2013 | Huey et al. |
| 2002/0077653 A1 | 6/2002 | Hudson et al. |
| 2002/0197302 A1 | 12/2002 | Cochrum et al. |
| 2003/0018357 A1 | 1/2003 | Luthra et al. |
| 2003/0133990 A1 | 7/2003 | Hursey et al. |
| 2003/0175333 A1 | 9/2003 | Shefer et al. |
| 2003/0176828 A1 | 9/2003 | Buckman et al. |
| 2003/0199922 A1 | 10/2003 | Buckman |
| 2003/0208150 A1 | 11/2003 | Bruder et al. |
| 2003/0212357 A1 | 11/2003 | Pace |
| 2004/0005350 A1 | 1/2004 | Looney et al. |
| 2004/0038893 A1 | 2/2004 | Ladner et al. |
| 2004/0121438 A1 | 6/2004 | Quirk |
| 2004/0166172 A1 | 8/2004 | Rosati et al. |
| 2004/0169033 A1 | 9/2004 | Kuibira et al. |
| 2004/0243043 A1 | 12/2004 | McCarthy et al. |
| 2005/0023956 A1 | 2/2005 | Kwak et al. |
| 2005/0058721 A1 | 3/2005 | Hursey |
| 2005/0070693 A1 | 3/2005 | Hansen et al. |
| 2005/0074505 A1 | 4/2005 | Hursey |
| 2005/0107826 A1 | 5/2005 | Zhu et al. |
| 2005/0118230 A1 | 6/2005 | Hill et al. |
| 2005/0119112 A1 | 6/2005 | Pfenninger et al. |
| 2005/0137512 A1 | 6/2005 | Campbell et al. |
| 2005/0143689 A1 | 6/2005 | Ramsey, III |
| 2005/0246009 A1 | 11/2005 | Toner et al. |
| 2005/0248270 A1 | 11/2005 | Ghosh et al. |
| 2005/0249899 A1 | 11/2005 | Bonutti |
| 2006/0034935 A1 | 2/2006 | Pronovost et al. |
| 2006/0078628 A1 | 4/2006 | Koman et al. |
| 2006/0116635 A1 | 6/2006 | Van Heugten |
| 2006/0121101 A1 | 6/2006 | Ladizinsky |
| 2006/0141018 A1 | 6/2006 | Cochrum et al. |
| 2006/0141060 A1 | 6/2006 | Hursey et al. |
| 2006/0159733 A1 | 7/2006 | Pendharkar et al. |
| 2006/0172000 A1 | 8/2006 | Cullen et al. |
| 2006/0178609 A1 | 8/2006 | Horn et al. |
| 2006/0193905 A1 | 8/2006 | Ehringer et al. |
| 2006/0211965 A1 | 9/2006 | Horn et al. |
| 2006/0211971 A1 | 9/2006 | Horn et al. |
| 2006/0271094 A1 | 11/2006 | Hudson et al. |
| 2006/0282046 A1 | 12/2006 | Horn et al. |
| 2007/0016152 A1 | 1/2007 | Karpowicz et al. |
| 2007/0031515 A1 | 2/2007 | Stucky et al. |
| 2007/0065491 A1 | 3/2007 | Huey et al. |
| 2007/0104768 A1 | 5/2007 | Huey et al. |
| 2007/0104792 A1 | 5/2007 | Jenkins |
| 2007/0134293 A1 | 6/2007 | Huey et al. |
| 2007/0142783 A1 | 6/2007 | Huey et al. |
| 2007/0154509 A1 | 7/2007 | Wilcher et al. |
| 2007/0154510 A1 | 7/2007 | Wilcher et al. |
| 2007/0154564 A1 | 7/2007 | Stucky et al. |
| 2007/0160638 A1 | 7/2007 | Mentkow et al. |
| 2007/0160653 A1 | 7/2007 | Fischer et al. |
| 2007/0167971 A1 | 7/2007 | Huey et al. |

(56) References Cited

U.S. PATENT DOCUMENTS

| | | |
|---|---|---|
| 2007/0251849 A1 | 11/2007 | Lo et al. |
| 2007/0275073 A1 | 11/2007 | Huey et al. |
| 2007/0276308 A1 | 11/2007 | Huey et al. |
| 2007/0276345 A1 | 11/2007 | Huey et al. |
| 2007/0281011 A1 | 12/2007 | Jenkins et al. |
| 2008/0027365 A1 | 1/2008 | Huey |
| 2008/0085300 A1 | 4/2008 | Huey et al. |
| 2008/0097271 A1 | 4/2008 | Lo et al. |
| 2008/0125686 A1 | 5/2008 | Lo |
| 2008/0146984 A1 | 6/2008 | Campbell et al. |
| 2008/0199539 A1 | 8/2008 | Baker et al. |
| 2008/0206134 A1 | 8/2008 | Lo et al. |
| 2008/0254146 A1 | 10/2008 | Huey et al. |
| 2008/0254147 A1 | 10/2008 | Huey et al. |
| 2008/0269658 A1 | 10/2008 | Vinton et al. |
| 2008/0299226 A1 | 12/2008 | Mentkow et al. |
| 2008/0317831 A1 | 12/2008 | Lo |
| 2008/0319476 A1 | 12/2008 | Ward et al. |
| 2009/0008261 A1 | 1/2009 | Kotzeva et al. |
| 2009/0018479 A1 | 1/2009 | McCarthy et al. |
| 2009/0043268 A1 | 2/2009 | Eddy et al. |
| 2009/0047366 A1 | 2/2009 | Bedard et al. |
| 2009/0053288 A1 | 2/2009 | Eskridge, Jr. et al. |
| 2009/0074880 A1 | 3/2009 | Ladizinsky |
| 2009/0076475 A1 | 3/2009 | Ross et al. |
| 2009/0112170 A1 | 4/2009 | Wells et al. |
| 2009/0162406 A1 | 6/2009 | Basadonna et al. |
| 2009/0186013 A1 | 7/2009 | Stucky |
| 2009/0186071 A1 | 7/2009 | Huey et al. |
| 2009/0232902 A1 | 9/2009 | Liu et al. |
| 2009/0274769 A1 | 11/2009 | Fregonese |
| 2009/0299253 A1 | 12/2009 | Hursey |
| 2010/0035045 A1 | 2/2010 | McAmish |
| 2010/0121244 A1 | 5/2010 | Horn et al. |
| 2010/0184348 A1 | 7/2010 | McAmish |
| 2010/0209531 A2 | 8/2010 | Stucky et al. |
| 2010/0228174 A1 | 9/2010 | Huey |
| 2010/0233248 A1 | 9/2010 | Huey et al. |
| 2011/0015565 A1 | 1/2011 | Hursey |
| 2011/0059287 A1 | 3/2011 | McAmish |
| 2011/0064785 A1 | 3/2011 | Daniels |
| 2011/0150973 A1 | 6/2011 | Bowlin et al. |
| 2011/0268784 A1 | 11/2011 | Huey |
| 2012/0004636 A1 | 1/2012 | Lo |
| 2012/0070470 A1 | 3/2012 | Pahari |
| 2012/0130296 A1 | 5/2012 | Huey |
| 2013/0041332 A1 | 2/2013 | Huey |
| 2013/0079695 A1 | 3/2013 | Huey et al. |

FOREIGN PATENT DOCUMENTS

| | | |
|---|---|---|
| CN | 101104080 | 1/2008 |
| EP | 0 107 051 | 9/1983 |
| EP | 0 296 324 | 12/1988 |
| EP | 0 353 710 | 2/1990 |
| EP | 0 826 822 | 3/1998 |
| EP | 0 888 783 A1 | 7/1999 |
| EP | 1 159 972 A2 | 5/2001 |
| EP | 1 714 642 | 10/2006 |
| GB | 2 259 858 | 3/1993 |
| GB | 2 314 842 | 1/1998 |
| JP | 61145120 | 7/1986 |
| JP | 01-096558 | 10/1987 |
| JP | 2-45040 | 2/1990 |
| JP | 9-504719 | 5/1997 |
| JP | 2777279 B2 | 7/1998 |
| JP | 10-337302 | 12/1998 |
| JP | 11-178912 | 7/1999 |
| JP | 11-332909 A1 | 7/1999 |
| JP | 2002-530157 | 9/2002 |
| JP | 2003-66045 | 3/2003 |
| JP | 2004123651 | 7/2006 |
| WO | WO 95/05445 | 2/1995 |
| WO | WO 95/12371 | 5/1995 |
| WO | WO 96/40285 | 12/1996 |
| WO | WO 99/13918 | 3/1999 |
| WO | WO 00/30694 | 6/2000 |
| WO | WO 00/66086 | 11/2000 |
| WO | WO 01/82896 | 8/2001 |
| WO | WO 01/97826 | 12/2001 |
| WO | WO 02/30479 | 4/2002 |
| WO | WO 02/060367 | 8/2002 |
| WO | WO 02/074325 | 9/2002 |
| WO | WO 03/074566 | 9/2003 |
| WO | WO 2005/012493 | 2/2005 |
| WO | WO 2005/030279 | 4/2005 |
| WO | WO 2005/087280 | 9/2005 |
| WO | WO 2005/123170 | 12/2005 |
| WO | WO 2006/006140 | 1/2006 |
| WO | WO 2006/012218 | 2/2006 |
| WO | WO 2006/088912 | 8/2006 |
| WO | WO 2006/110393 | 10/2006 |
| WO | WO 2007/120342 | 10/2007 |
| WO | WO 2008/036225 | 3/2008 |
| WO | WO 2008/127497 | 10/2008 |
| WO | WO 2009/109194 | 9/2009 |

OTHER PUBLICATIONS

U.S. Appl. No. 13/682,085, filed Nov. 20, 2012, including prosecution history.

Wagner, Holly, "Topical Oxygen Helps Hard-To-Heal Wounds Heal Faster and Better," Jan. 28, 2003, obtained from http://researchnews.osu.edu/archive/oxvwound.htm.

Dictionary of Traditional Chinese Medicine, "Astringents and Haemostatices," The Commercial Press, LTD., Apr. 1984 [ISBN 962 07 3051 8], pp. 216-217, total 4 pages.

Hempen, et al., A Materia Medica for Chinese Medicine, Plants minerals and animal products, Churchill Livingston Elsevier, 2009, [ISBN 978 0 443 10094 9], pp. 832-833 (*Halloysitum rubrum*, Chi shi zi), total 5 pages.

Hsu, et al. Orintal Materia Medica—a concise guide, pp. 310-311, 612-613, 32-34, total 12 pages. Oriental Healing Arts Institute, 1986. [ISBN 0 941 942 22 8].

Huang, Pharmacology of Chinese Herbs, Second Edition, p. 243 (Antidiarrheal Herbs), total 3 pages. CRC Press 1999. [ISBN 0 8493 1665 0].

Li, et al. Chinese Materia Medica—Combinations and Applications, Donica Publishing Ltd., 2002, [ISBN 1 901149 02 1], p. 622 (Ch. 18 Herbs for Promoting Astriction), total 5 pages.

Soine et al., Roger's Inorganic Pharmaceutical Chemistry, Lea & Febiger 1967, p. 462-463 (Aluminum and Aluminum Compounds), [QV744 S683r 1967] total 5 pages.

Wu, Jing-Nuan, "An Illustrated Chinese Materia Medica," Oxford University Press, Inc. 2005 (13 pages).

Xinrong, Traditional Chinese Medicine, A Manual from A-Z, Symptoms, Therapy and Herbal Remedies, [ISBN 3 540 42846 1], p. 470 (total 3 pages), Springer-Verlag Berlin Heidelberg 2003.

Yanchi, The Essential Book of Traditional Chinese Medicine, vol. 2: Clinical Practice, p. 155-157 (Traditional Chinese Prescriptions) 142-143 (Chinese Medicinal Herbs) total 8 pages. [ISBN 0 231 06518 3 9v.2] 1988.

U.S. Appl. No. 13/759,963, filed Feb. 5, 2013, including prosecution history.

"Mastering the Art of Innovative Thinking," (color brochure) FMC BioPolymer, 2001 FMC Corporation.

Alam, et al., Application of a Zeolite Hemostatic Agent Achieves 100% Survival in a Lethal Model of Complex Groin Injury in Swine, May 2004, The Journal of Trauma Injury, Infection, and Critical Care, vol. 56, pp. 974-983.

Aldrich—Handbook of Fine Chemicals and Laboratory Equipment, 2000-2001, pp. 1177-1178.

Analgesics and Anti-inflammatory agents 2004, retrieved from the internet on May 26, 2010, URL: http://web.archive.org/web/20040904151322/http://faculty.weber.edu/ewalker/Medicinal_Chemistry/topics/Analgesia_antiinflam/Analgesics_anti-inflamitory.htm.

Angeloni, V., M.D.: "How to care for your wound.", Heartland Dermatology & Skin Cancer P. C., copyright 2001, V. Angeloni MD.

(56) References Cited

OTHER PUBLICATIONS

Army halts use of new first aid item to study more, Seattle PI, Dec. 24, 2008.
Army halts use of WoundStat, http://stripes.com, Apr. 23, 2009.
Army pulls anti clotting agent after Fort Sam study finds threat, MySanAntonio Military, Dec. 24, 2008.
Baker, Sarah E. et al., Controlling Bioprocesses with Inorganic Surfaces: Layered Clay Hemostatic Agents, Department of Chemistry and Biochemistry, University of California, Santa Barbara, American Chemical Association 2007, 19, pp. 4390-4392 (3 pages total).
Basadonna, G., et al.: "A novel kaolin coated surgical gauze improves hemostasis both in vitro and in vivo", Journal of Surgical Research, vol. 144, No. 2, Feb. 2008, p. 440, XP002534658, abstract.
Bethesda, MD, TraumaCure, Life-saving News for Battlefield Soldiers & Wounded Civilians FDA Clears Product to Stop Severe Bleeding, Sep. 10, 2007.
Butenas—Mechanism of factor Vlla-dependent coagulation in hemophilia blood, Hemostasis, Thrombosis, and Vascular Biology, BLOOD, Feb. 1, 2002—vol. 99, No. 3.
Caloplast (Kaoline Poultrice), South African Electronic Package Inserts, Information presented by Malahyde Information Systems, Copyright 1996-1998, printed from home.intekom.com/pharm/allied/caloplst.html#INDICATIONS, two pages.
Carraway, et al., Comparison of a new mineral based hemostatic agent to a commercially available granular zeolite agent for hemostasis in a swine model of lethal extremity arterial hemorrhage, Resuscitation vol. 78, Issue 2, Aug. 2008.
Clay makers (raw materials) retrieved from the internet on Mar. 15, 2010, URL: http://web.archive.org/web/20020609175053/http://www.claymaker.com/ceramic_central/info/raw_clays.htm (year 2002, pp. 104).
Comparative Testing of Hemostatic Dressings in a Severe Groin Hemorrhage, Trauma & Resuscitative Medicine Department, NMRC, Aug. 2008 (Part 1 of 3, pp. 1-9).
Comparative Testing of Hemostatic Dressings in a Severe Groin Hemorrhage, Trauma & Resuscitative Medicine Department, NMRC, Aug. 2008 (Part 2 of 3, pp. 10-19).
Comparative Testing of Hemostatic Dressings in a Severe Groin Hemorrhage, Trauma & Resuscitative Medicine Department, NMRC, Aug. 2008 (Part 3 of 3, pp. 20-29).
Curasorb Calcium Alginate Dressings information page, http://www.kendallhq.com/kendallhealthcare/pageBuilder.aspx?webPageID=0&topicID=70966&xs1=xs1/productPagePrint.xsl (last accessed May 22, 2012).
Davis et al., 1H—NMR Study of Na Alginates Extracted from *Sargassum spp.* In Relation to Metal Biosorption, 110 Applied Biochemistry and Biotechnology 75 (2003).
Fruijtier-Polloth, "The safety of synthetic zeolites used in detergents", Arch Toxicol (2009) 83:23-25.
Galan, et al.: "Technical properties of compound kaolin sample from griva (Macedonia, Greece)", Applied Clay Science 1996 10:477-490.
Gibbar-Clements, et al.: "The Challenge of Warfarin Therapy", JSTOR: The American Journal of Nursing,vol. 100, No. 3 (Mar. 2000), pp. 38-40.
Griffin, John H., Role of surface in surface-dependent activation of Hageman factor (blood coagulation Factor XII), Proc. Natl. Acad. Sci. USA vol. 75, No. 4, Apr. 1978, pp. 1998-2002 (5 pages total).
Hahn, Lynn: "High temperature 1H NMR to determine the relative amounts of guluronate and mannuronate in the sodium alginate sample", Intertek, ASA, Analytical Report, Report No. 60665 v 1, dated May 6, 2012.
HemCon Medical Technologies Inc. 501(k) Summary, GhitoGauze, Mar. 20, 2009.
Hollister Wound Care Restor Calcium Alginate Dressing, Silver instruction manual and information booklet, available at http://hollisterwoundcare.com/files/pdfs/ifus/Restore907814B407ColorBreak.pdf (last accessed May 22, 2012).
James, "Silver Copper Zeolite Guinea Pig Sensitization Study—Beuhler Method", Data Evaluation Report dated Oct. 3, 1989.
Kheirabadi, Army Assessment of New Hemostatic Products Suitable for Treating Combat Wounds, US Army Institute of Surgical Research, Aug. 11, 2008.
Kheirabadi, et al., Session IV-B, Paper 28, 8:20 a.m., Comparison of New Hemostatic Dressings with Currently Deployed Hemcon Bandage in a Model of Extremity Arterial Hemorrhage in Swine, Jan. 2009.
Kheirabadi, et al., The Journal of TRAUMA Injury, Infection, and Critical Care, Comparison of New Hemostatic Granules/Powders with Currently Deployed Hemostatic Products in a Lethal model of Extremity Arterial Hemorrhage in Swine, Feb. 2009, pp. 316-328.
Kheirabadi, Final Report, Title: Assessment of Efficacy of New Hemostatic Agents in a Model of Extremity Arterial Hemorrhage in Swine, U.S. Army Institute of Surgical Research, Ft. Sam Houston, TX 78234, Mar. 4, 2008.
Kovzun, I. G., et al.: "Application of nanosize clay-mineral systems in the complex therapy for hemophilia "A" patients", Database HCAPLUS [online], XP002534657, retrieved from STN Database accession No. 2009:502758 abstract & Nanosistemi, Nanomateriali, Nanotekhnologii, vol. 6, No. 2, 2008.
Lin et al., Synthesis of Hybridized Polyacrylic Acid-Kaolin Material and Its Superwater Absorbent Performance, J. Huangiao Univ. (Nat. Sci.) Mar. 2000.
Long et al., Synthesis of Bentonite-superabsorbent Composite, J. Guilin Inst. Tech., Feb. 2004.
Macrina, VCU's Research Enterprise, Structure and Resources, Oct. 23, 2008.
Manugel® GMB alginate, FMC BioPolymer, Know how. It works. sm Product Specifications, 2011 FMC Corporation.
Margolis, "Initiation of Blood Coagulation by Glass and Related Surfaces", J. Physiol. (1957) 137, 95-109.
Margolis, J., The Kaolin Clotting Time: A Rapid One-Stage Method for Diagnosis of Coagulation Defects, J. Clin. Pathol 1958, 11, pp. 406-409 (5 pages total).
Medline Maxorb Extra AG Silver Alginate, http://www.medicaldepartmentstore.com/Medline-Maxorb-p/1560.htm (last accessed May 22, 2012).
Okada, et al.: "Preparation of zeolite-coated cordierite honeycombs prepared by an in situ crystallization method", Science and Technology of Advanced Materials 2004 5:479-484.
O'Reilly et al.: "Studies on Coumarin Anticoagulant Drugs—Initiaion of Warfarin Therapy Without a Loading Dose", Circulation by the American Heart Association, http://circ.ahajournals.org, 1968, 38, 169-177.
Ore-Medix, Traumastat Hemostatic Bandage, Aug. 7, 2008.
Permanent suspension of Woundstat use, https://email.z-medica.com, Apr. 17, 2009.
Reprinted related contents of U.S. Alaract regarding QuikClot Combat Gauze, Apr. 2009.
Sadler et al.: "Biochemstry and Genetics of Van Willebrand Factor", Annual Review of Biochemistry; 1998. 67:395-424.
Scott Sackinger's Medical Devices Professional Summary dated Mar. 2009.
Sinter. (2004). In the New Penguin Dictionary of Science. London: Penguin. Retrieved May 7, 2009, from http://www.credoreference.com/entry/7463549/.
Tactical Combat Casualty Care Guidelines, Feb. 2009.
TraumaCure, Innovative Wound Care Products for Wound Care Solutions, Apr. 24, 2009.
Vitrify—(2001). In Chambers 21s5t Century Dictionary. London. Chambers Harrap. Retrieved May 7, 2009, from http://www.credoreference.com/entry/1236485/.
Vlok, Marie E.: "Kaoline poultice", Manual of Nursing, vol. 1, Basic Nursing, revised ninth edition, p. 269. Copyright Juta & Co, Ltd., Lansdowne, South Africa, first published 1962.
Wound Stat, http://shadowspear.com/vb/showthread.php?t=16586 dated Dec. 22, 2008, last accessed Apr. 16, 2009.
WoundStat found to be potentially hazardous, Army News, news from Iraq . . . , http://armytimes.com/news/2009/04/army_woundstat_042009w/, posted Apr. 20, 2009, last accessed Apr. 20, 2009.

(56) References Cited

OTHER PUBLICATIONS

Wright, J. Barry et al.: "Wound management in an era of increasing bacterial antibiotic resistance: A role for topical silver treatment", American Journal of Infection Control, vol. 26 (6), 1998, pp. 572-577.

Z-Medica Corporation 510(k) Summary, QuikClot eX, Oct. 4, 2007.

Alam, et al., Comparative Analysis of Hemostatic Agents in a Swine Model of Lethal Groin Injury, Jun. 2003, The Journal of Trauma Injury, Infection, and Critical Care, vol. 54, No. 6, pp. 1077-1082.

Dyer, A. et al. "Diffusion in heteroionic zeolites: part 1. Diffusion of water in heteroionics natrolites." Microporous and Mesoporous Materials. 1998. pp. 27-38. vol. 21.

Gielen, M., Solid State Organometallic Chemistry: Methods and Applications Physical Organometallic Chemistry, 1999, New York John Wiley & Sons, Ltd. (UK), V. 2, p. 156.

Hursey, et al., Bandage Using Molecular Sieves, Apr. 18, 2002, International Application Published Under the PCT, WO 02/30479 A1.

IMA-EU, Kaolin, Oct. 2006, p. 1-2.

Le Van Mao, Raymond et al. "Mesporous Aluminosilicates prepared from Zeolites by Treatment with Ammonium Fluorosilicate." J. Mater. Chem. 1993. pp. 679-683. vol. 3, No. 6.

The Merck Index; 1989, pp. 1596-1597, abstract 10021.

Voet, Donald & Judith: "Molecular Physiology", Biochemistry, p. 1087-1096, vol. 64, 1990, John Wiley & Sons.

Ward, et al., The Journal of TRAUMA Injury, Infection, and Critical Care, Comparison of a New Hemostatic Agent to Current Combat Hemostatic Agents in a Swine Model of Lethal Extremity Arterial Hemorrhage, Aug. 2007, pp. 276-284.

Wright, J.K. et al. "Thermal Injury Resulting from Application of a GranularMineral Hemostatic Agent." The Journal of TRAUMA Injury, Infection, and Critical Care. 2004. pp. 224-230. vol. 57, No. 2.

U.S. Appl. No. 12/352,513, filed Jan. 12, 2009 including prosecution history.

U.S. Appl. No. 60/668,022, filed Apr. 4, 2005, including prosecution history.

U.S. Appl. No. 60/708,206, filed Aug. 15, 2005, including prosecution history.

U.S. Appl. No. 60/902,738, filed Feb. 21, 2007, including prosecution history.

U.S. Appl. No. 60/955,854, filed Aug. 14, 2007, including prosecution history.

U.S. Appl. No. 11/054,918, filed Feb. 9, 2005 including prosecution history.

U.S. Appl. No. 12/555,876, filed Sep. 9, 2009, including prosecution history.

U.S. Appl. No. 13/598,381, filed Aug. 29, 2012, including prosecution history.

U.S. Appl. No. 11/592,477, filed Nov. 2, 2006 including prosecution history.

U.S. Appl. No. 13/595,932, filed Aug. 27, 2012, including prosecution history.

U.S. Appl. No. 11/634,673, filed Dec. 5, 2006 including prosecution history.

U.S. Appl. No. 11/590,427, filed Oct. 30, 2006 including prosecution history.

U.S. Appl. No. 12/417,802, filed Apr. 3, 2009 including prosecution history.

U.S. Appl. No. 13/115,699, filed May 25, 2011 including prosecution history.

U.S. Appl. No. 13/593,310, filed Aug. 23, 2012, including prosecution history.

U.S. Appl. No. 12/611,830, filed Nov. 3, 2009, including prosecution history.

U.S. Appl. No. 13/526,431, filed Jun. 18, 2012 including prosecution history.

U.S. Appl. No. 11/633,687, filed Dec. 4, 2006 including prosecution history.

U.S. Appl. No. 11/654,409, filed Jan. 17, 2007, including prosecution history.

U.S. Appl. No. 11/715,057, filed Mar. 6, 2007 including prosecution history.

U.S. Appl. No. 12/581,782, filed Oct. 19, 2009 including prosecution history.

U.S. Appl. No. 10/939,869, filed Sep. 13, 2004 including prosecution history.

U.S. Appl. No. 12/510,203, filed Jul. 27, 2009 including prosecution history.

U.S. Appl. No. 11/082,716, filed Mar. 16, 2005 including prosecution history.

U.S. Appl. No. 11/303,607, filed Dec. 16, 2005 including prosecution history.

U.S. Appl. No. 11/404,126, filed Apr. 13, 2006 including prosecution history.

U.S. Appl. No. 11/586,968, filed Oct. 25, 2006 including prosecution history.

U.S. Appl. No. 10/939,687, filed Sep. 13, 2004 including prosecution history.

U.S. Appl. No. 11/023,869, filed Dec. 27, 2004 including prosecution history.

U.S. Appl. No. 11/544,238, filed Oct. 6, 2006 including prosecution history.

U.S. Appl. No. 11/584,079, filed Oct. 20, 2006 including prosecution history.

U.S. Appl. No. 11/606,617, filed Nov. 29, 2006 including prosecution history.

U.S. Appl. No. 11/710,106, filed Feb. 22, 2007 including prosecution history.

U.S. Appl. No. 12/101,336, filed Apr. 11, 2008 including prosecution history.

U.S. Appl. No. 12/101,346, filed Apr. 11, 2008 including prosecution history.

U.S. Appl. No. 11/634,531, filed Dec. 6, 2006 including prosecution history.

U.S. Appl. No. 12/140,356, filed Jun. 17, 2008 including prosecution history.

U.S. Appl. No. 12/204,129, filed Sep. 4, 2008 including prosecution history.

U.S. Appl. No. 12/503,481, filed Jul. 15, 2009 including prosecution history.

U.S. Appl. No. 13/240,795, filed Sep. 22, 2011, including prosecution history.

U.S. Appl. No. 13/175,380, filed Jul. 1, 2011, including prosecution history.

Webster's Dictionary definition of "expose" (1993).

DEVICES AND METHODS FOR THE DELIVERY OF BLOOD CLOTTING MATERIALS TO BLEEDING WOUNDS

CROSS-REFERENCE TO RELATED APPLICATIONS

This application is a continuation of U.S. patent application Ser. No. 11/592,477, filed Nov. 2, 2006, entitled "Devices and methods for the delivery of blood clotting materials to bleeding wounds," which is a continuation-in-part application of U.S. patent application Ser. No. 11/054,918, filed Feb. 9, 2005, entitled "Devices and methods for the delivery of molecular sieve materials for the formation of blood clots." The contents of all of the above-referenced applications are incorporated herein by reference in their entireties.

TECHNICAL FIELD

The present invention relates generally to blood clotting devices and, more particularly, to blood clotting materials, devices incorporating such materials, and methods for the delivery of such materials for use as bleeding control devices.

BACKGROUND OF THE INVENTION

Blood is a liquid tissue that includes red cells, white cells, corpuscles, and platelets dispersed in a liquid phase. The liquid phase is plasma, which includes acids, lipids, solubilized electrolytes, and proteins. The proteins are suspended in the liquid phase and can be separated out of the liquid phase by any of a variety of methods such as filtration, centrifugation, electrophoresis, and immunochemical techniques. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can be wounded. Often bleeding is associated with such wounds. In some circumstances, the wound and the bleeding are minor, and normal blood clotting functions in addition to the application of simple first aid are all that is required. Unfortunately, however, in other circumstances substantial bleeding can occur. These situations usually require specialized equipment and materials as well as personnel trained to administer appropriate aid. If such aid is not readily available, excessive blood loss can occur. When bleeding is severe, sometimes the immediate availability of equipment and trained personnel is still insufficient to stanch the flow of blood in a timely manner.

Moreover, severe wounds can often be inflicted in remote areas or in situations, such as on a battlefield, where adequate medical assistance is not immediately available. In these instances, it is important to stop bleeding, even in less severe wounds, long enough to allow the injured person or animal to receive medical attention.

In an effort to address the above-described problems, materials have been developed for controlling excessive bleeding in situations where conventional aid is unavailable or less than optimally effective. Although these materials have been shown to be somewhat successful, they are sometimes not effective enough for traumatic wounds and tend to be expensive. Furthermore, these materials are sometimes ineffective in some situations and can be difficult to apply as well as remove from a wound.

Additionally, or alternatively, the previously developed materials can produce undesirable side effects. For example, prior art blood clotting material is generally a powder or a fine particulate in which the surface area of the material often produces an exothermic reaction upon the application of the material to blood. Oftentimes excess material is unnecessarily poured onto a wound, which can exacerbate the exothermic effects. Depending upon the specific attributes of the material, the resulting exothermia may be sufficient to cause discomfort to or even burn the patient. Although some prior art patents specifically recite the resulting exothermia as being a desirable feature that can provide clotting effects to the wound that are similar to cauterization, there exists the possibility that the tissue at and around the wound site may be undesirably impacted.

Furthermore, to remove such materials from wounds, irrigation of the wound is often required. If an amount of material is administered that causes discomfort or burning, the wound may require immediate flushing. In instances where a wounded person or animal has not yet been transported to a facility capable of providing the needed irrigation, undesirable effects or over-treatment of the wound may result.

Bleeding can also be a problem during surgical procedures. Apart from suturing or stapling an incision or internally bleeding area, bleeding is often controlled using a sponge or other material used to exert pressure against the bleed site and/or absorb the blood. However, when the bleeding becomes excessive, these measures may not be sufficient to stop the flow of blood. Moreover, any highly exothermic bleed-control material may damage the tissue surrounding the bleed site and may not be configured for easy removal after use.

Based on the foregoing, it is a general object of the present invention to provide devices for controlling bleeding and methods of their use that overcome or improve upon the prior art.

SUMMARY OF THE INVENTION

According to one aspect, the present invention resides in an apparatus for promoting the clotting of blood, thereby controlling bleeding. The apparatus comprises a receptacle for retaining a blood clotting material in particulate form therein. At least a portion of the receptacle is defined by a mesh having openings therein such that when the apparatus is applied to a bleed site, the particulate blood clotting material comes into contact with blood through the openings. A zeolite powder is incorporated into the mesh to facilitate the blood clotting qualities when the apparatus is applied to a bleeding wound.

Other aspects of the present invention include a pad for controlling bleeding and a bandage applicable to a bleeding wound. In both the pad and the bandage, there is a mesh structure and particles of blood clotting material retained therein. The mesh structure impregnated with or otherwise includes zeolite powder. In the pad embodiment, there is a rigid or semi-rigid support attached to the mesh structure to facilitate the application of pressure to the pad and the wound. In the bandage, there is a flexible substrate attached to the mesh structure, the substrate being a cloth or plastic member that may be adhesively attached to cover a wound. In any embodiment, the mesh structure may be defined by a plurality of members (strands, filaments, or strips of synthetic or natural material) interconnected and arranged to define openings. The openings are sized to allow contact to be maintained between the particles of the blood clotting material and blood.

An advantage of the present invention is that upon completion of the application of any of the devices of the present invention to a bleeding wound, the devices can be easily removed. In particular, because the blood clotting material is zeolite or oxidized cellulose in granule, bead, or pellet form and encased in a pouch or mesh structure, the material can be cleanly pulled away from the treated wound and disposed of. Accordingly, little or no irrigation of the wound is required to flush away remaining blood clotting material. In devices in which the pouch containing blood clotting material is incorporated into an adhesive bandage, the device can be left on the wound for the amount of time necessary to cause clotting.

Another advantage is that the particlized form of zeolite used as the blood clotting material allows the material to react less exothermically with blood. As the particle size increases (e.g., from fine to coarse), the surface area of the particles that the blood can come into contact with decreases. The porous nature of the zeolite still allows liquid blood constituents to be wicked away to cause thickening of the blood, thereby facilitating the formation of clots. Because the particle surface area exposed to the blood is reduced, a less aggressive drawing of moisture from the blood is realized, which thereby tempers the exothermic effects experienced at the wound site.

With regard to embodiments in which zeolite powder is included in the mesh, one advantage is that the contacting surface area between the powder and the tissue of the wound site is increased. In particular, the flow of blood to the mesh results in immediate clotting effects because a time delay due to the blood having to flow around the mesh material to the blood clotting material is avoided.

Still another advantage of the present invention is that the proper dose of blood clotting material can be readily applied to an open wound. Particularly when the device is a porous pouch containing zeolite or oxidized cellulose, the device can be readily removed from sterilized packaging and held directly at the points from which blood emanates to facilitate clotting of the blood without spilling powder or pellets outside the wound area. Guesswork, estimation, or calculation of the amounts of blood clotting material for application to a bleeding wound is eliminated. Accordingly, little or no blood clotting material is wasted.

DETAILED DESCRIPTION OF THE PREFERRED EMBODIMENTS

Figure 1:
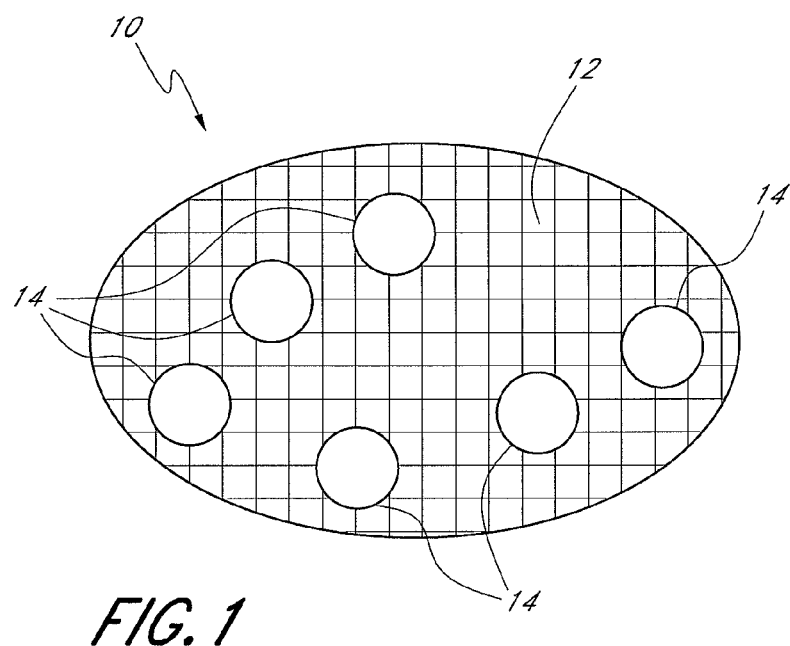
FIG. 1 is a schematic representation of a blood clotting device of the present invention.

Disclosed herein are devices and methods for delivering materials to wounds to promote the clotting of blood and the dressing of the wounds. The devices generally comprise expedients or apparatuses that can be applied to bleeding wounds such that the materials contact the tissue of the wound to minimize or stop blood flow of blood by absorbing at least portions of the liquid phases of the blood, thereby promoting clotting. One apparatus comprises a receptacle for retaining molecular sieve material in particulate form or oxidized cellulose material in particulate form therein. At least a portion of the receptacle is defined by a mesh having openings therein, and at least a portion of the particulate molecular sieve material or oxidized cellulose material is in direct contact with blood through the openings. As used herein, the terms "particle" and "particulate" are intended to refer to balls, beads, pellets, rods, granules, polymorphous shapes, and combinations of the foregoing.

In embodiments incorporating a molecular sieve material as the blood clotting material, the molecular sieve material used in the present invention may be a synthetic polymer gel, cellulosic material, porous silica gel, porous glass, alumina, hydroxyapatite, calcium silicate, zirconia, zeolite, or the like. Exemplary synthetic polymers include, but are not limited to, stylene-divinylbenzene copolymer, cross-linked polyvinyl alcohol, cross-linked polyacrylate, cross-linked vinyl ether-maleic anhydride copolymer, cross-linked stylene-maleic anhydride copolymer or cross-linked polyamide, and combinations thereof.

The molecular sieve material is preferably a zeolite. Other molecular sieve materials that may be used include, but are not limited to, faujasite. As used herein, the term "zeolite" refers to a crystalline form of aluminosilicate having the ability to be dehydrated without experiencing significant changes in the crystalline structure. The zeolite may include one or more ionic species such as, for example, calcium and sodium moieties. Typically, the zeolite is a friable material that is about 90% by weight calcium and about 10% by weight sodium. The calcium portion contains crystals that are about 5 angstroms in size, and the sodium portion contains crystals that are about 4 angstroms in size. The preferred molecular structure of the zeolite is an "A-type" crystal, namely, one having a cubic crystalline structure that defines round or substantially round openings.

The zeolite may be mixed with or otherwise used in conjunction with other materials having the ability to be dehydrated without significant changes in crystalline structure. Such materials include, but are not limited to, magnesium sulfate, sodium metaphosphate, calcium chloride, dextrin, a polysaccharide, combinations of the foregoing materials, and hydrates of the foregoing materials.

Zeolites for use in the disclosed applications may be naturally occurring or synthetically produced. Numerous varieties of naturally occurring zeolites are found as deposits in sedimentary environments as well as in other places. Naturally occurring zeolites that may be applicable to the compositions described herein include, but are not limited to, analcite, chabazite, heulandite, natrolite, stilbite, and thomosonite. Synthetically produced zeolites that may also find use in the compositions and methods described herein are generally produced by processes in which rare earth oxides are substituted by silicates, alumina, or alumina in combination with alkali or alkaline earth metal oxides.

Various materials may be mixed with, associated with, or incorporated into the zeolites to maintain an antiseptic environment at the wound site or to provide functions that are supplemental to the clotting functions of the zeolites. Exemplary materials that can be used include, but are not limited to, pharmaceutically-active compositions such as antibiotics, antifungal agents, antimicrobial agents, anti-inflammatory agents, analgesics (e.g., cimetidine, chlorpheniramine maleate, diphenhydramine hydrochloride, and promethazine hydrochloride), bacteriostatics, compounds containing silver ions, and the like. Other materials that can be incorporated to provide additional hemostatic functions include ascorbic acid, tranexamic acid, rutin, and thrombin. Botanical agents having desirable effects on the wound site may also be added.

In embodiments incorporating oxidized cellulose as the blood clotting material, the oxidized cellulose used in the present invention is a chemically oxidized form of a common cellulose fiber such as cotton and is also known as cellulosic acid, absorbable cellulose, or polyanhydroglucuronic acid. The degree of oxidation of the fiber is a function of the carboxylation content of the fibrous cellulose material. In particular, as the number of carboxyl groups on the cellulose structure is increased, the oxidation content correspondingly increases. Oxidized cellulose may be manufactured by the action of nitrogen dioxide gas ($NO_2$) on cellulose fiber. Other methods of manufacturing oxidized cellulose include oxidation of cellulose fiber with aqueous oxidizing agents such as hypochlorite salts, although the use of such agents is less preferred than the use of nitrogen dioxide gas.

In one embodiment of the present invention, a device for facilitating the clotting of blood directly at a wound site is shown with reference to FIG. 1. The device is a permeable pouch that allows liquid to enter to contact blood clotting zeolite (or other molecular sieve material) or oxidized cellulose material retained therein. Although the devices of the present invention are described hereinafter as including zeolite as the blood clotting agent, it should be understood that the blood clotting agent may be oxidized cellulose. Sealed packaging (not shown) provides a sterile environment for storing the device until it can be used. The device, which is shown generally at 10 and is hereinafter referred to as "pouch 10," comprises a screen or mesh 12 and zeolite particles 14 retained therein by the screen or mesh. The mesh 12 is closed on all sides and defines openings that are capable of retaining the zeolite particles 14 therein while allowing liquid to flow through. As illustrated, the mesh 12 is shown as being flattened out, and only a few zeolite particles 14 are shown.

The zeolite particles 14 are substantially spherical or irregular in shape (e.g., balls, beads, pellets, or the like) and about 0.2 millimeters (mm) to about 10 mm in diameter, preferably about 1 mm to about 7 mm in diameter, and more preferably about 2 mm to about 5 mm in diameter. In any embodiment (balls, beads, pellets, etc.), less particle surface area is available to be contacted by blood as the particle size is increased. Therefore, the rate of clotting can be controlled by varying the particle size. Furthermore, the adsorption of moisture (which also has an effect on the exothermic effects of the zeolite) can also be controlled.

The mesh 12 is defined by interconnected strands, filaments, or strips of material. The strands, filaments, or strips can be interconnected in any one or a combination of manners including, but not limited to, being woven into a gauze, intertwined, integrally-formed, and the like. Preferably, the interconnection is such that the mesh can flex while substantially maintaining the dimensions of the openings defined thereby. The material from which the strands, filaments or strips are fabricated may be a polymer (e.g., nylon, polyethylene, polypropylene, polyester, or the like), metal, fiberglass, or an organic substance (e.g., cotton, wool, silk, or the like).

Figure 2:
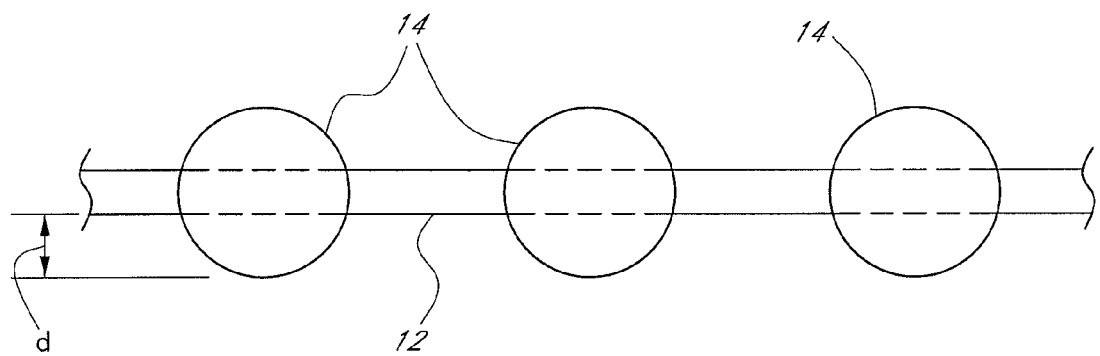
FIG. 2 is a side view of the blood clotting device of FIG. 1 illustrating the retaining of blood clotting particles in a mesh container.

Referring now to FIG. 2, the openings defined by the mesh 12 are dimensioned to retain the zeolite particles 14 but to accommodate the flow of blood therethrough. Because the mesh 12 may be pulled tight around the zeolite particles 14, the particles may extend through the openings by a distance d. If the zeolite particles 14 extend through the openings, the particles are able to directly contact tissue to which the pouch 10 is applied. Thus, blood emanating from the tissue immediately contacts the zeolite particles 14, and the water phase thereof is wicked into the zeolite material, thereby facilitating the clotting of the blood. However, it is not a requirement of the present invention that the zeolite particles protrude through the mesh.

To apply the pouch 10 to a bleeding wound, the pouch is removed from the packaging and placed on the bleeding wound. The zeolite particles 14 in the mesh 12 contact the tissue of the wound and/or the blood, and at least a portion of the liquid phase of the blood is adsorbed by the zeolite material, thereby promoting the clotting of the blood.

Figure 3:
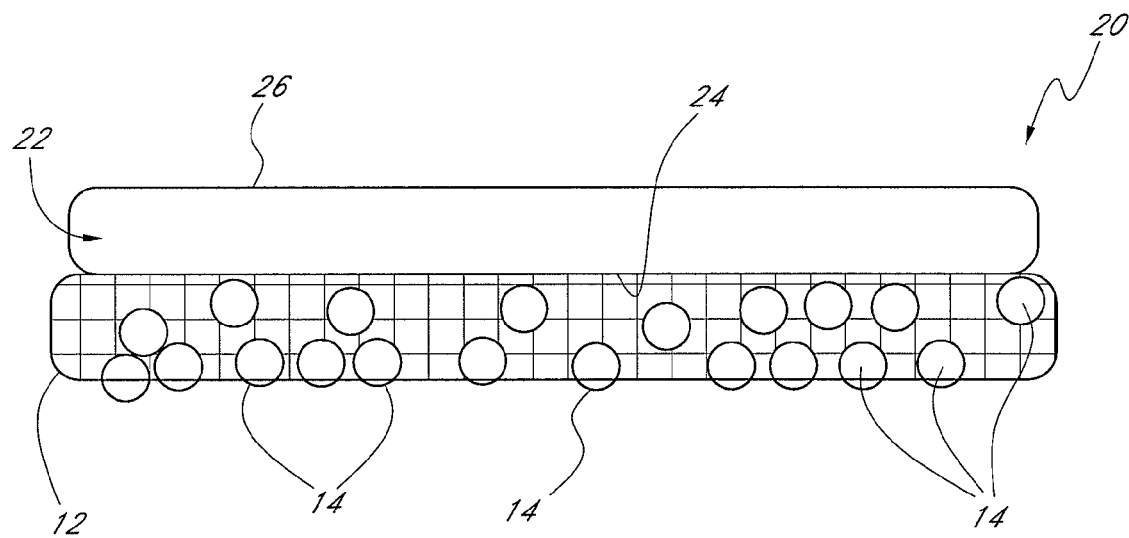
FIG. 3 is a side view of a pressure pad incorporating the blood clotting particles encapsulated in a mesh container for pressure application to a bleeding wound.

Another embodiment of the present invention is a pad which is shown at 20 with reference to FIG. 3 and is hereinafter referred to as "pad 20." The pad 20 comprises the mesh 12, zeolite (or other molecular sieve) particles 14 (or oxidized cellulose particles) retained therein by the mesh 12, and a support 22 to which pressure may be applied in the application of the pad 20 to a bleeding wound. The mesh 12, as above, has openings that are capable of retaining the zeolite particles 14 therein while allowing the flow of blood therethrough.

The mesh 12 is stitched, glued, clamped, or otherwise mounted to the support 22. The support 22 comprises an undersurface 24 against which the zeolite particles 14 are held by the container 12 and a top surface 26. The undersurface 24 is impermeable to the zeolite particles 14 (migration of the particles into the support 22 is prevented) and is further resistant to the absorption of water or other fluids. The top surface 26 is capable of having a pressure exerted thereon by a person applying the pad 20 to a bleeding wound or by a weight supported on the top surface 26. The entire support 22 is rigid or semi-rigid so as to allow the application of pressure while minimizing discomfort to the patient.

To apply the pad 20 to a bleeding wound, the pad 20 is removed from its packaging and placed on the bleeding wound. As with the pouch of the embodiment of FIGS. 1 and 2, the zeolite particles 14 are either in direct contact with the tissue of the wound or are in direct contact with the blood. Pressure may be applied to the wound by pressing on the top surface 26 with a hand or by placing a weight on the surface, thereby facilitating the contact between the zeolite particles 14 and the wound and promoting the adsorption of the liquid phase of the blood. The pad 20 (with or without a weight) may also be held onto the wound using a strapping device such as a belt, an elastic device, hook-and-loop material, combinations of the foregoing devices and materials, and the like.

Figure 4:
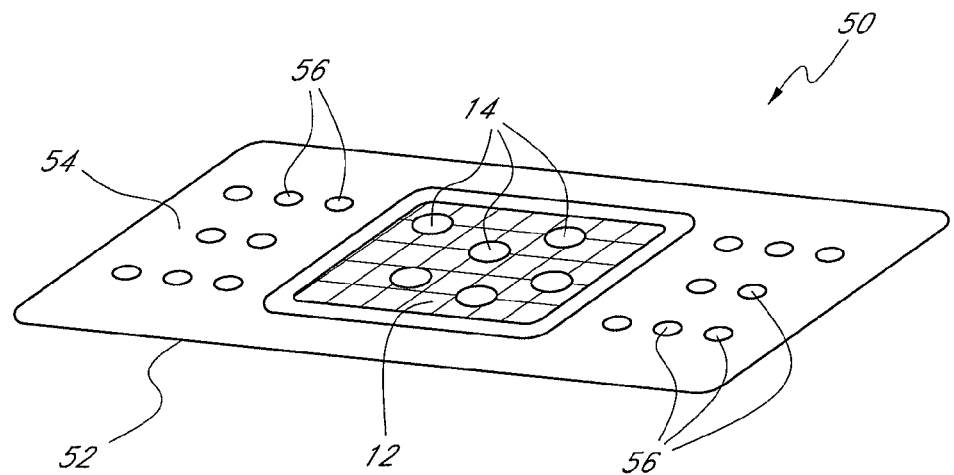
FIG. 4 is a perspective view of a bandage incorporating the blood clotting particles in a mesh container for application to a bleeding wound.

Referring now to FIG. 4, another embodiment of the present invention is a bandage, shown at 50, which comprises zeolite particles 14 (or some other molecular sieve material or oxidized cellulose in particle form) retained in a mesh 12 and mounted to a flexible substrate 52 that can be applied to a wound (for example, using a pressure-sensitive adhesive to adhere the bandage 50 to the skin of a wearer). The mesh 12 is stitched, glued, or otherwise mounted to a substrate 52 to form the bandage 50.

The substrate 52 is a plastic or a cloth member that is conducive to being retained on the skin of an injured person or animal on or proximate a bleeding wound. An adhesive 54 is disposed on a surface of the substrate 52 that engages the skin of the injured person or animal. Particularly if the substrate 52 is a non-breathable plastic material, the substrate may include holes 56 to allow for the dissipation of moisture evaporating from the skin surface.

Figure 5:
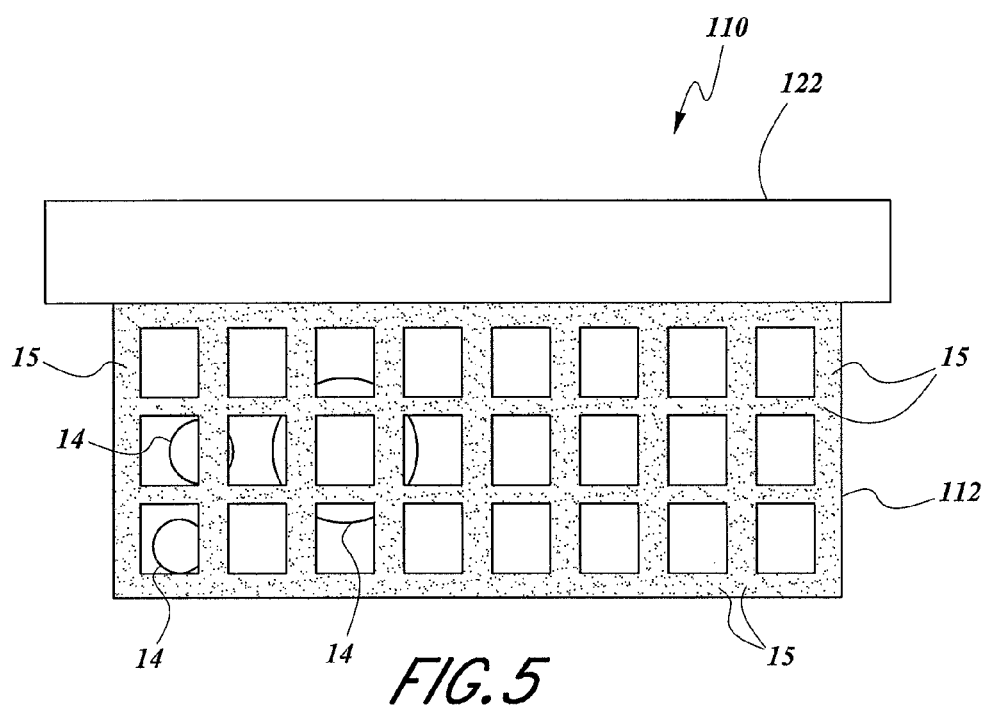
FIG. 5 is a side view of a blood clotting device incorporating blood clotting particles retained in a mesh impregnated with zeolite particles.

Referring now to FIG. 5, another embodiment of the present invention comprises a device 110 having the zeolite particles 14 (or other blood clotting material such as oxidized cellulose) as described above retained within a fabric pouch. The fabric pouch is a zeolite-impregnated mesh 112 having hemostatic qualities, namely, the hemostatic properties of zeolite. The device 110 may include a support 122, thereby defining a pad. When the device 110 is a pad, the support 122 provides a surface at which pressure may be applied in the application of the device to a bleeding wound. Without the support 122, the device 110 may be used as a surgical sponge.

The zeolite-laden mesh 112 is defined by interconnected strands, filaments, or strips of material that are interconnected by being woven, intertwined, or integrally formed as in the above-disclosed embodiments. The mesh 112 includes particles of zeolite powder 15. Although the particles of zeolite powder 15 are shown as being concentrated along portions of the edges of the mesh 112, it should be understood that the zeolite powder is dispersed throughout the material from which the mesh is fabricated. Preferably, the interconnection of the strands, filaments, or strips to form the mesh 112 is such that the device 110 can flex while substantially maintaining the dimensions of the openings, thereby allowing the zeolite particles 14 to be retained.

Figure 6:
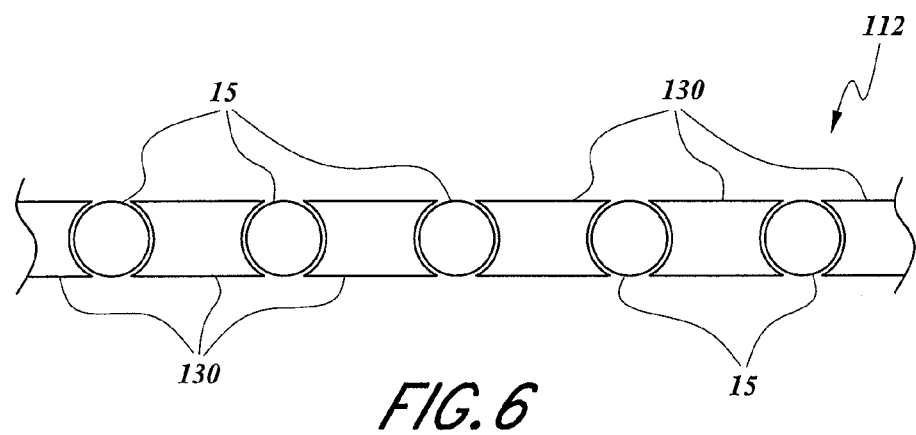
FIG. 6 is a side view of one embodiment of the mesh of the device of FIG. 5.
Figure 7:
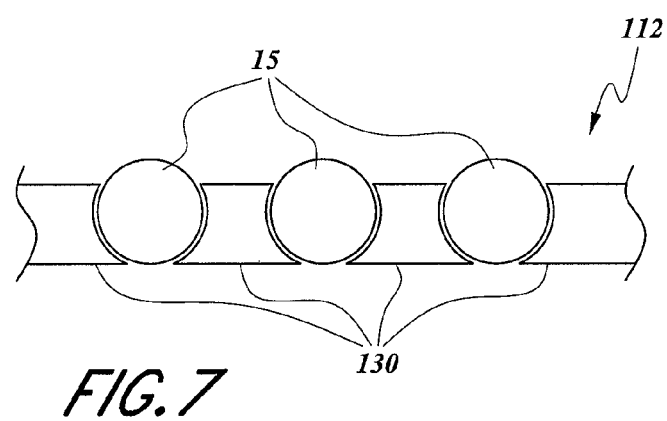
FIG. 7 is a side view of another embodiment of the mesh of the device of FIG. 5.

Referring now to FIGS. 6 and 7, zeolite is impregnated into or otherwise retained by the material of the strands, filaments, or strips that define the mesh 112. In particular, the particles of zeolite powder 15 may be captured within a matrix material 130 such that the particles contact the bleeding tissue when the strands, filaments, or strips defining the mesh 112 are brought into contact with the wound. The present invention is not limited to zeolite impregnated or incorporated into the material of the mesh, however, as other materials such as oxidized cellulose may be impregnated or incorporated into the mesh material. As is shown in FIG. 6, the zeolite powder 15 may be captured and held within the outer surface of the matrix material 130. In such an embodiment, the matrix material 130 is preferably sufficiently porous to facilitate the flow of blood therethrough, thus allowing liquid phases of the blood to be at least partially absorbed by the zeolite powder 15 prior to contacting the zeolite particles (or other molecular sieve materials) retained in the mesh 112. As is shown in FIG. 7, the zeolite powder may be captured so as to protrude above the surface of the matrix material 130.

Figure 8:
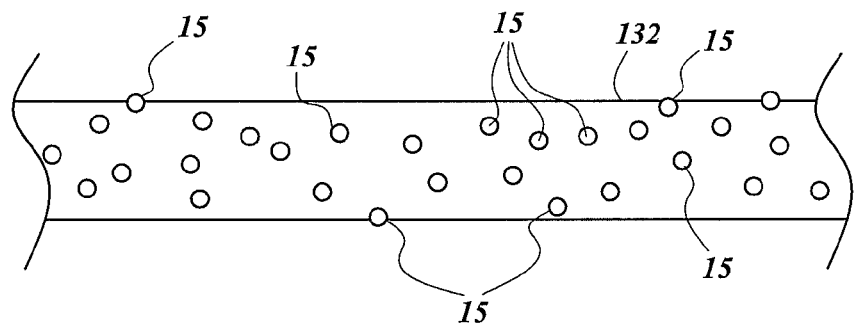
FIG. 8 is a side view of another embodiment of the mesh of the device of FIG. 5.

Referring to FIG. 8, the zeolite powder 15 may be impregnated into a substrate material 132 and retained therein by any suitable method. In the impregnation of the zeolite powder 15 into the substrate material 132, the substrate material is generally sufficiently soft (e.g., fluid when exposed to heat) to allow for its deformation to accommodate the zeolite powder. The zeolite powder 15 may be impregnated completely into the substrate material 132, or it may be partially impregnated so as to extend out of the substrate material.

In either the embodiment of FIGS. 6 and 7 or of FIG. 8, the matrix material or the substrate material may be a polymer (e.g., nylon, polyethylene, polypropylene, polyester, or the like), metal, fiberglass, or an organic substance (e.g., cotton, wool, silk, or the like). The matrix material or the substrate material may also be cellulose or a cellulose derivative.

Figure 9:
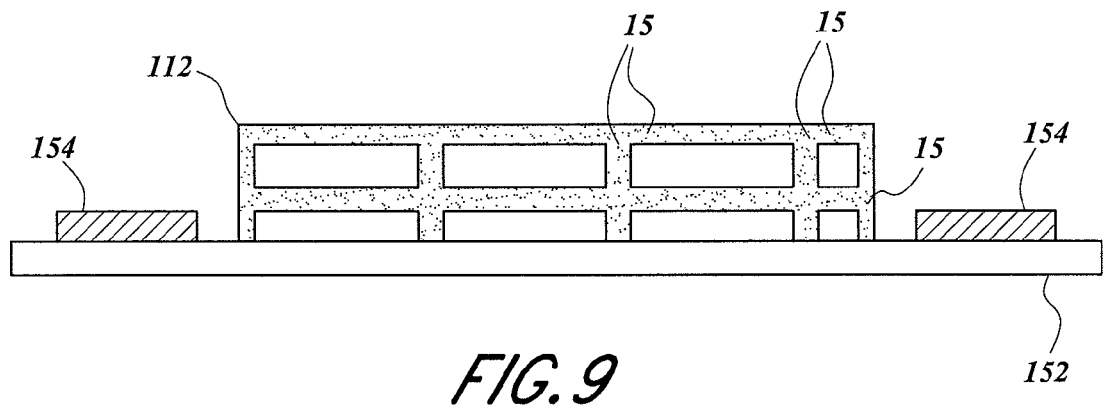
FIG. 9 is a side view of a bandage incorporating blood clotting particles retained in a zeolite-impregnated mesh material.

The zeolite-laden mesh 112 may be utilized in conjunction with a bandage, as is shown in FIG. 9. The mesh 112 (which comprises the zeolite powder 15) may be mounted to a flexible substrate 152 that can be applied to a wound in a manner similar to that described above with reference to FIG. 4. The mesh 112 may be stitched, glued, or otherwise mounted to the substrate 152, which may be a plastic or cloth member that is retained on the skin of an injured person or animal on or proximate the bleeding wound (e.g., via an adhesive 154).

In the preparation of zeolite material for the devices of the present invention (i.e., formation of the material into particle form), an initial level of hydration of the zeolite may be controlled by the application of heat to the zeolite material either before or after the material is formed into particles. However, it has also surprisingly been found that as the particle size of the zeolite is increased, the moisture content has less of a correlative effect on any exothermia produced as the result of mixing the particlized zeolite in blood. As such, formation of the zeolite material into the zeolite particles (shown at 14 in FIGS. 1-4), may be by extrusion, milling, casting, or the like.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

What is claimed is:

1. An apparatus for promoting the clotting of blood, comprising:
 a pouch closed on all sides, the pouch comprising a first blood clotting material in powder form; and
 a second blood clotting material in loose particulate form retained in the pouch;
 wherein a portion of the first blood clotting material in powder form is exposed on a surface of the pouch, and
 wherein the pouch further comprises a mesh having openings that are sufficiently large to allow at least a portion of the second blood clotting material to extend through the openings to allow contact with blood outside of the pouch.

2. The apparatus of claim 1, wherein the first blood clotting material comprises a zeolite.

3. The apparatus of blood of claim 2, wherein the zeolite comprises particles having diameters of about 0.2 mm to about 10 mm.

4. The apparatus of blood of claim 2, wherein the zeolite comprises particles having diameters of about 1 mm to about 7 mm.

5. The apparatus of blood of claim 2, wherein the zeolite comprises particles having diameters of about 2 mm to about 5 mm.

6. The apparatus of claim 1, wherein the mesh is flexible.

7. The apparatus of blood of claim 1, wherein one or both of the first and second blood clotting materials is a molecular sieve material.

8. An apparatus for promoting the clotting of blood, comprising:
 a pouch closed on all sides, the pouch having a first blood clotting material in powder form applied thereto; and
 a second blood clotting material in loose particulate form retained in the pouch;
 wherein a portion of the first blood clotting material in powder form is exposed on a surface of the pouch, and
 wherein the pouch further comprises a mesh having openings that are sufficiently large to allow at least a portion of the second blood clotting material to extend through the openings to allow contact with tissue of a bleeding wound outside of the pouch.

9. The apparatus of claim 8, wherein the first blood clotting material comprises a zeolite.

10. The apparatus of blood of claim 9, wherein the zeolite comprises particles having diameters of about 0.2 mm to about 10 mm.

11. The apparatus of blood of claim 9, wherein the zeolite comprises particles having diameters of about 1 mm to about 7 mm.

12. The apparatus of blood of claim 9, wherein the zeolite comprises particles having diameters of about 2 mm to about 5 mm.

13. The apparatus of blood of claim 8, wherein the mesh is flexible.

14. The apparatus of blood of claim 8, wherein one or both of the first and second blood clotting materials is a molecular sieve material.

15. A method of accelerating the clotting of blood in a bleeding wound comprising:
   providing an apparatus comprising:
      a mesh pouch closed on all sides, the mesh pouch comprising a first blood clotting material in powder form,
      a second blood clotting material in loose particulate form retained in the pouch,
      wherein a portion of the first blood clotting material in powder form is exposed on a surface of the pouch, and wherein the pouch further comprises a mesh having openings that are sufficiently large to allow at least a portion of the second blood clotting material to extend through the openings to allow contact with blood outside of the pouch;
   applying the apparatus to the bleeding wound; and
   maintaining the apparatus at the bleeding wound at least until blood from the wound begins to clot.

16. The method of claim 15, wherein the first blood clotting material comprises a zeolite.

17. The method of claim 16, wherein the zeolite comprises particles having diameters of about 0.2 mm to about 10 mm.

18. The method of claim 16, wherein the zeolite comprises particles having diameters of about 1 mm to about 7 mm.

19. The method of claim 16, wherein the zeolite comprises particles having diameters of about 2 mm to about 5 mm.

20. The method of claim 15, wherein the mesh is flexible.

21. The method of claim 15, further comprising applying pressure to the apparatus while the apparatus is applied to the bleeding wound.

22. The apparatus of blood of claim 15, wherein one or both of the first and second blood clotting materials is a molecular sieve material.

* * * * *